United States Patent [19]

Barner et al.

[11] 4,268,453

[45] May 19, 1981

[54] PROCESS FOR THE MANUFACTURE OF CHOLESTENE DERIVATIVES AND NOVEL INTERMEDIATES IN THEIR MANUFACTURE

[75] Inventors: Richard Barner, Witterswil; Josef Hübscher, Seon, both of Switzerland

[73] Assignee: Hoffmann-La Roche Inc., Nutley, N.J.

[21] Appl. No.: 146,880

[22] Filed: May 5, 1980

[30] Foreign Application Priority Data

May 18, 1979 [CH] Switzerland .......................... 4676/79

[51] Int. Cl.³ ................................................ C07J 1/00
[52] U.S. Cl. ......................... 260/397.5; 260/239.55 R; 260/397.2
[58] Field of Search ............................ 260/395.7, 397.1

[56] References Cited

U.S. PATENT DOCUMENTS 3,856,780 12/1974 Narwid et al. .................... 260/397.5
4,134,904 1/1979 Kaiser ............................. 260/397.1

OTHER PUBLICATIONS

Steroids (1971), No. 17, pp. 649–652, relied on.
J. Fluorine Chem. (1976), No. 8, pp. 209–221.

*Primary Examiner*—Elbert L. Roberts
*Attorney, Agent, or Firm*—Jon S. Saxe; Bernard S. Leon; James H. Callwood

[57] ABSTRACT

The present disclosure is directed to 6-lower alkoxy-25,26-(lower alkyl or lower alkylene)methylene dioxy-3,5-cyclocholest-22-ene derivatives which are useful in the manufacture of 25,26-dihydroxycholecalciferol.

2 Claims, No Drawings

PROCESS FOR THE MANUFACTURE OF CHOLESTENE DERIVATIVES AND NOVEL INTERMEDIATES IN THEIR MANUFACTURE

DESCRIPTION OF THE INVENTION

The present disclosure is directed to a process for the manufacture of cholestene derivatives which can be used as intermediates in the manufacture of 25,26-dihydroxycholecalciferol.

The cholestene derivatives obtained in accordance with the present invention have the general formula

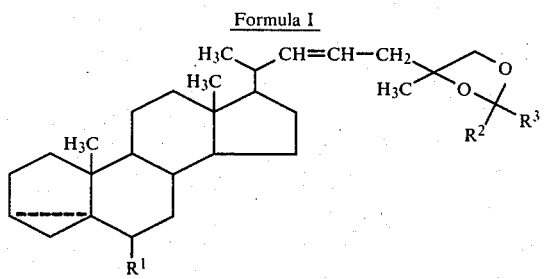

Formula I wherein $R^1$ is lower alkoxy; and $R^2$ and $R^3$ each is lower alkyl; or $R^2$ and $R^3$ together are lower alkylene.

As used throughout the specification and appended claims, the terminology "lower alkyl" means $C_{1-6}$ aliphatic hydrocarbons. Examples of lower alkyl groups denoted by $R^2$ and $R^3$ are methyl, ethyl and propyl, with methyl being preferred.

The term "lower alkylene" means a divalent aliphatic hydrocarbon radical containing 1-6 carbon atoms. Examples of lower alkylene groups formed by $R^2$ and $R^3$ taken together are ethylene and propylene.

The term "lower alkoxy" means a lower alkyl group attached to the remainder of the molecule by an oxygen atom. Examples of lower alkoxy groups denoted by $R^1$ are $C_{1-6}$ alkoxy groups, especially methoxy.

The process provided by the present invention comprises reacting a compound of the general formula

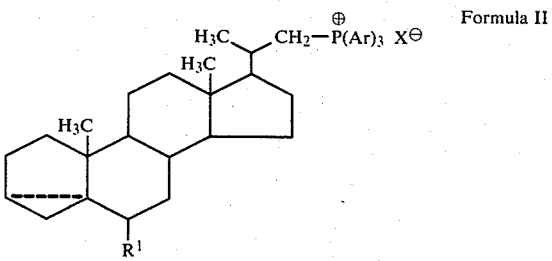

Formula II wherein $R^1$ is as above; Ar is aryl; and $X^\ominus$ is an anion, in a Wittig reaction with a compound of the general formula

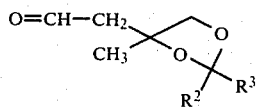

Formula III wherein $R^2$ and $R^3$ are as above.

As used throughout the specification and appended claims, the term "aryl" means an aromatic organic radical derived by the removal of one hydrogen atom from an aromatic hydrocarbon which can be unsubstituted or substituted by one or more lower alkyl or alkoxy substituents. Examples of aryl groups denoted by Ar are phenyl optionally substituted by lower alkyl or lower alkoxy, preferably phenyl.

The term "anion" means the negatively-charged atom liberated at the anode during electrolysis. Examples of anions denoted by $X^\ominus$ are halogen ions, preferably iodide.

The reaction can be carried out under conditions which are known for Wittig reactions. Examples of solvents which can be used are ethers such as tetrahydrofuran, dioxan and diethyl ether or hydrocarbons such as toluene. Examples of bases which can be used are butyl lithium, sodium hydride, sodium amide or potassium tert.butylate.

The manufacture of the ylid is preferably carried out at a low temperature (e.g., at $-50°$ C. to $-80°$ C.) in order to avoid the possibility of cleaving the i-steroid grouping.

The invention is also concerned with the novel compounds of formula II.

The compounds of formula II can be prepared in accordance with the invention by reacting a compound of the general formula

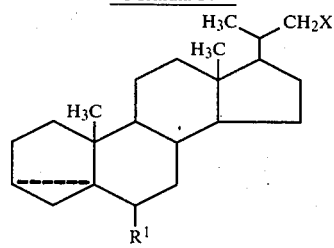

Formula IV wherein X is halogen; and $R^1$ is a lower alkoxy, with a triarylphosphine in the presence of a base in an inert organic solvent while heating.

Since the compounds of formula II begin to be unstable at temperatures above 100° C., the reaction is conveniently carried out at a temperature up to 100° C. in a solvent in which a sufficient reaction velocity is achieved at such temperatures. The preferred solvent is acetonitrile. A compound which is capable of binding traces of hydrogen halide possibly present is conveniently used as the base. Such a base which can readily be separated from the reaction mixture, for example, potassium carbonate which is poorly soluble in acetonitrile, is preferably used.

The cholestene derivatives of formula I can be converted by hydrogenation of the double bond into corresponding cholestane derivatives which, after ketal cleavage and retro-i-rearrangement, yield 25,26-dihydroxycholesterol. The latter can be converted in a known manner into 25,26-dihydroxycholecalciferol.

The hydrogenation of the double bond in a cholestene derivative of formula I can be carried out catalytically, for example, in the presence of noble metals such as platinum, palladium or rhodium or in the presence of nickel catalysts.

The retro-i-rearrangement can be carried out by treatment with an acid in a suitable solvolytic medium. The solvolytic medium can be, for example, an aqueous medium which contains a miscible co-solvent. Suitable co-solvents are ethereal solvents such as tetrahydrofuran or dioxan, ketones such as acetone and and methyl ethyl ketone or alcohols such as ethanol. Examples of acids which can be used are mineral acids such as hydrochloric acid, hydrobromic acid and sulphuric acid or organic sulphonic acids such as benzenesulphonic acid and p-toluenesulphonic acid. When these acids are used, the ketal group is simultaneously hydrolyzed.

The thus-obtained 25,26-dihydroxycholesterol can be converted into 25,26-dihydroxycholecalciferol, for example, as described in Steroids 24 (1974), page 463.

The following examples illustrate the present invention:

EXAMPLE 1

9.35 g of (20S)-21-iodo-6β-methoxy-20-methyl-3α,5-cyclo-5α-pregnane, 6.64 g of triphenylphosphine and 6.6 g of powdered potassium carbonate were vigorously stirred in 17 ml of acetonitrile for 12 hours at 100° C. (bath temperature). 10 ml of acetonitrile were distilled off from the suspension which was then stirred at 100° C. for 6 hours. The mixture was stirred with 300 ml of acetone, filtered, the residue was washed with acetone, and the filtrate was concentrated. The viscous oil obtained was stirred with ether, crystallization occurring. The crystals were filtered off and washed with ether. For purification, the phosphonium salt (13.25 g) was dissolved in 175 ml of acetone and again precipitated with 500 ml of ether. The crystals were filtered off, washed with ether and dried in a high vacuum. There were obtained 11.7 g (79.5%) of [(20S)-6β-methoxy-20-methyl-3α,5-cyclo-5α-pregnan-21-yl]-triphenylphosphonium iodide of melting point 230°–231° C.

EXAMPLE 2

3.75 ml of a 2 M solution of butyl lithium in hexane were added dropwise under a nitrogen atmosphere at −78° C. to a suspension of 3.59 g of [(20S)-6β-methoxy-20-methyl-3α,5-cyclo-5α-pregnan-21-yl]-triphenylphosphonium iodide in 100 ml of dry tetrahydrofuran. For the complete formation of the ylid, the mixture was stirred for a further 0.5 hour at −78° C. and for 0.5 hour at −25° C., a deep orange-red solution being obtained. At unaltered temperature 790 mg of (±)-2,2,4-trimethyl-1,3-dioxolane-4-acetaldehyde (86% according to gas chromatography) were added while stirring, and the mixture was subsequently stirred for a further 30 minutes at −20° C., for 1 hour at 0° C. and for 1 hour at room temperature. Then, the mixture was taken up with 200 ml of ice water and 200 ml of ether, the ether phase was separated in a separating funnel, and the aqueous phase was back-extracted three times with 200 ml of ether each time. The combined ether phases were dried over magnesium sulphate and concentrated on a rotary evaporator. The residue was chromatographed on silica gel with toluene/ethyl acetate (2:1), 1.48 g (73%) of 6β-methoxy-24-[2,2,4-trimethyl-1,3-dioxolan-4-yl]-22-dehydro-3α,5-cyclo-5α-cholane being obtained. This compound can be converted into 25,26-dihydrocholesterol as follows:

A solution of 1.29 g of 6β-methoxy-24-[2,2,4-trimethyl-1,3-dioxolan-4-yl]-22-dehydro-3α-5-cyclo-5α-cholane in 50 ml of ethyl acetate was hydrogenated over 0.8 g of 10% platinum carbon at room temperature (1 hour; hydrogen uptake 79 ml). The catalyst was filtered off, and the filtrate was evaporated to give 6β-methoxy-24-[2,2,4-trimethyl-1,3-dioxolan-4yl]-3α,5-cyclo-5α-cholane.

7.8 g of 6β-methoxy-24-[2,2,4-trimethyl-1,3-dioxolan-4-yl]-3α,5-cyclo-5α-cholane were dissolved in 200 ml of dioxan, and, after adding 0.3 g of p-toluenesulphonic acid and 60 ml of water, the mixture was heated to reflux for 3 hours. The mixture was then stirred at room temperature for 12 hours and treated with 200 ml of ether. The aqueous phase was washed twice with 50 ml of ether, and the combined organic phases were dried over magnesium sulphate and evaporated. The residue was suspended in ether, the suspension was filtered, and the residue was washed with ether. After drying the residue, there were obtained 3.6 g of 25,26-dihydroxycholesterol of melting point 173°–176° C.; $[\alpha]_D = -35.8°$ (C=0.4% in methanol).

What is claimed is:

1. Compounds of the general formula

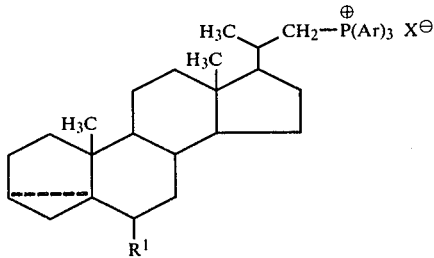

wherein $R^1$ is lower alkoxy; Ar is aryl; and $X^\ominus$ is an anion.

2. [(20S)-6β-methoxy-20-methyl-3α,5-cyclo-5α-pregnan-21-yl]-triphenylphosphonium iodide.